(12) United States Patent
Boyd et al.

(10) Patent No.: US 7,776,878 B2
(45) Date of Patent: Aug. 17, 2010

(54) HETEROCYCLIC BENZYLAMINO DERIVATIVES, THEIR MANUFACTURE AND USE AS PHARMACEUTICAL AGENTS

(75) Inventors: Edward Boyd, Reading (GB); Frederick Brookfield, Benson (GB); Jonathan Gridley, Reading (GB); Konrad Honold, Penzberg (DE); Raymond Lau, Bracknell (GB); Stefan Scheiblich, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 382 days.

(21) Appl. No.: 11/989,272

(22) PCT Filed: Jul. 28, 2006

(86) PCT No.: PCT/EP2006/007479

§ 371 (c)(1),
(2), (4) Date: Jan. 22, 2008

(87) PCT Pub. No.: WO2007/014707

PCT Pub. Date: Feb. 8, 2007

(65) Prior Publication Data

US 2010/0120840 A1    May 13, 2010

(30) Foreign Application Priority Data

Aug. 1, 2005   (EP) .................. 05016641

(51) Int. Cl.
*A01N 47/00* (2006.01)
*A61K 31/26* (2006.01)
(52) U.S. Cl. .................. 514/303; 544/127; 546/256; 546/118
(58) Field of Classification Search .................. None
See application file for complete search history.

(56) References Cited

FOREIGN PATENT DOCUMENTS

| WO | WO 99/21859 | 5/1999 |
|---|---|---|
| WO | WO 03/035065 | 5/2003 |
| WO | WO 2004/016611 | 2/2004 |
| WO | WO 2004/024897 | 3/2004 |
| WO | WO 2005/063747 | 7/2005 |
| WO | WO 2006066913 A2 * | 6/2006 |
| WO | WO 2007/014707 | 2/2007 |

OTHER PUBLICATIONS

Sawyer et al., Expert Opin. Investig. Drugs (2001), 10(7): 1327-1344.

* cited by examiner

*Primary Examiner*—Brandon J Fetterolf
*Assistant Examiner*—Jean Cornet
(74) *Attorney, Agent, or Firm*—George W. Johnston; Patricia S. Rocha-Tramaloni; Gene J. Yao

(57) ABSTRACT

Objects of the present invention are the compounds of formula (I) their pharmaceutically acceptable salts, enantiomeric forms, diastereoisomers and racemates, the preparation of the above-mentioned compounds, pharmaceutical compositions containing them and their manufacture, as well as the use of the above-mentioned compounds in the control or prevention of illnesses such as cancer.

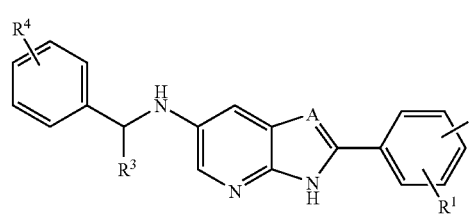

(I)

6 Claims, No Drawings

HETEROCYCLIC BENZYLAMINO DERIVATIVES, THEIR MANUFACTURE AND USE AS PHARMACEUTICAL AGENTS

This application is the national stage of International Application No. PCT/EP2006/007479, filed Jul. 28, 2006, which claims the benefit of European Application No. 05016641.2, filed Aug. 1, 2005, which is hereby incorporated by reference in its entirety.

This invention relates to heterocyclic benzylamino derivatives that inhibit the activity of protein kinases. Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration.

BACKGROUND OF THE INVENTION

Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489-495; Biscardi, J. S., et al., Adv. Cancer Res. 76 (1999) 61-119.

The tyrosine kinases are a class of protein kinases. The Src family which consists of at least eight members (Src, Fyn, Lyn, Yes, Lck, Fgr, Hck and Blk) that participate in a variety of signaling pathways represents the major family of cytoplasmic protein tyrosine kinases (Schwartzberg, P. L., Oncogene 17 (1998) 1463-1468). The prototypical member of this tyrosine kinase family is Src, which is involved in proliferation and migration responses in many cell types (Sawyer, T., et al., Expert Opin. Investig. Drugs 10 (2001) 1327-1344). Src activity has been shown to be elevated in different cancers, e.g. breast, colon (>90%), pancreatic (>90%) and liver (>90%) tumors. Highly increased Src activity is also associated with metastasis (>90%) and poor prognosis. Antisense Src message impedes growth of colon tumor cells in nude mice (Staley, C. A., Cell Growth Differ. 8 (1997) 269-274), suggesting that Src inhibitors could slow tumor growth. Furthermore, in addition to its role in cell proliferation, Src also acts in stress response pathways, including the hypoxia response. Nude mice studies with colon tumor cells expressing antisense Src message have reduced vascularization (Ellis, L. M., et al., J. Biol. Chem. 273 (1998) 1052-1057), which suggests that Src inhibitors could be anti-angiogenic as well as anti-proliferative.

Src disrupts E-cadherin associated cell-cell interactions (Avizienyte, E., et al., Nat. Cell Biol. 4 (2002) 632-638). A low molecular weight Src inhibitor prevents this disruption thereby reducing cancer cell metastasis (Nam, J. S., et al., Clin. Cancer Res. 8 (2002) 2430-2436).

Src inhibitors may prevent the secondary injury that results from a VEGF-mediated increase in vascular permeability such as that seen following stroke (Eliceiri, B. P., et al., Mol. Cell. 4 (1999) 915-924; Paul, R., et al., Nat. Med. 7 (2001) 222-227).

Blockade of Src prevents dissociation of the complex involving Flk, VE-cadherin, and β-catenin with the same kinetics with which it prevents VEGF-mediated VP/edema and account for the Src requirement in VEGF-mediated permeability and provide a basis for Src inhibition as a therapeutic option for patients with acute myocardial infarction (Weis, S., et al., J. Clin. Invest. 113 (2004) 885-894).

Src also plays a role in osteoporosis. Mice genetically engineered to be deficient in Src production were found to exhibit osteopetrosis, the failure to resorb bone (Soriano, P., et al., Cell 64 (1991) 693-702; Boyce, B. F., et al., J. Clin., Invest. 90 (1992) 1622-1627). This defect was characterized by a lack of osteoclast activity. Since osteoclasts normally express high levels of Src, inhibition of Src kinase activity may be useful in the treatment of osteoporosis (Missbach, M., et al., Bone 24 (1999) 437-449).

Low molecular weight inhibitors for protein kinases are widely known in the state of the art. For src inhibition such inhibitors are based on i.e. thieno-pyridine derivatives (US 2004/0242883); pyrido-pyrimidine derivatives (WO 04/085436); pyrido-pyrimidone derivatives (WO 04/041823); pyrimidine derivatives (WO 03/004492 and WO 01/00213); Quinazoline derivatives (WO 01/94341 and WO 02/016352); isoxazole derivatives (WO 02/083668) and pyrazole derivatives (WO 02/092573).

Some phenyl-aza-benzimidazoles are known as inhibitors of IgE-mediated immune response and suppressors of cytokines and leukocytes with antiproliferative effect from WO 04/024897. And some benzimidazole-pyrazoles and -indazoles are known as kinase inhibitors from WO 03/035065, especially as inhibitors against Kdr, Syk and Itk tyrosine kinases. WO 2005/063747 describes pyrrolo[2,3-b]pyridine derivatives as kinase inhibitors for the treatment of kinase associated diseases such as cancer, viral infections, Alzheimer's disease and the like.

SUMMARY OF THE INVENTION

The present invention relates to heterocyclic benzylamino derivatives of the general formula I

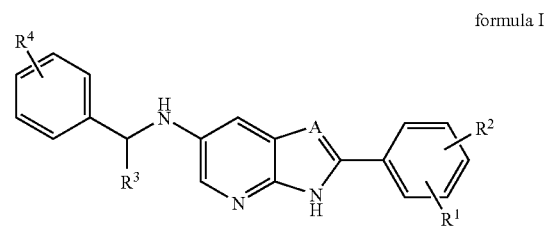

formula I wherein,
$R^1$ and $R^2$ independently represent hydrogen, halogen, alkyl, alkoxy, alkoxyalkoxy or acylamino;
$R^3$ is hydrogen or alkyl;
$R^4$ is hydrogen, halogen, alkoxy or alkyl;
A is =CH— or =N—;
and all pharmaceutically acceptable salts thereof.

The compounds according to this invention show activity as protein kinase inhibitors, in particular Src family tyrosine kinase inhibitors, and may therefore be useful for the treatment of diseases mediated by said tyrosine kinases.

Src family tyrosine kinases are known to be involved in a variety of disease states. Compounds of the present invention may be used as active agents in the prevention and therapy of, for example, transplant rejection, inflammatory bowel syndrome, rheumatoid arthritis, psoriasis, restenosis, allergic asthma, Alzheimer's disease, Parkinson, stroke, osteoporosis, benign hyperplasias and cancer including colon, breast, lung, prostate and pancreatic cancer and leukemia.

Objects of the present invention are the compounds of formula I and pharmaceutically acceptable salts and their enantiomeric forms, the preparation of the above-mentioned compounds, pharmaceutical compositions or medicaments containing them and their manufacture as well as the use of the above-mentioned compounds in the control or prevention of illnesses, especially of illnesses and disorders as mentioned above or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 6 carbon atoms, preferably from 1 to 4 carbon atoms, more preferably 1 or 2 carbon atoms, such as methyl, ethyl, n-propyl, isopropyl, n-butyl, 2-butyl, t-butyl.

As used herein, the term "alkoxy" means an alkyl group as defined above which is connected via an oxygen atom. Examples are e.g. methoxy, ethoxy, isopropoxy and the like.

As used herein, the term "alkoxyalkoxy" means an alkoxy group as defined above which is substituted by alkoxy. Examples are e.g methoxy-methoxy, ethoxy-methoxy, 2-methoxy-ethoxy, 2-ethoxy-ethoxy, 4-methoxy-butoxy, 2-methoxy-butoxy, 2-ethoxy-propoxy, 3-propoxy-butoxy, and the like, preferably 2-ethoxy-ethoxy.

As used herein, the term "acylamino" means an alkyl group as defined above which is attached via a —C(O)—NH— group. Examples are e.g acetylamino, propinonylamino, isobutyrylamino, n-buturylamino, 3-methyl-butyrylamino, pentanoylamino and the like.

As used herein, the term "halogen" means fluorine, chlorine, bromine and iodine, preferably fluorine, chlorine or bromine and more preferred fluorine and chlorine.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case, including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Preferably the position of $R^4$ in formula I is ortho to the —$CHR^3$—NH— linkage.

An embodiment of the invention are the compounds according to formula I, wherein $R^1$ is hydrogen, alkoxyalkoxy or acylamino;
$R^2$ is hydrogen; and
$R^4$ is hydrogen or alkyl.

Another embodiment of the invention are the compounds according to formula I, wherein
A is =N—.

Another embodiment of the invention are the compounds according to formula I, wherein
$R^1$ is hydrogen, alkoxyalkoxy or acylamino;
$R^2$ is hydrogen;
$R^4$ is hydrogen or alkyl; and
A is =N—.

Another embodiment of the invention are the compounds according to formula I, wherein
$R^1$ and $R^2$ independently represent hydrogen or alkyl;
$R^3$ is hydrogen or alkyl;
$R^4$ is hydrogen or alkyl; and
A is =N—.

Such a compound is for example:
(1-Phenyl-ethyl)-(2-phenyl-3H-imidazo[4,5-b]pyridin-6-yl)-amine.

Another embodiment of the invention are the compounds according to formula I, wherein
$R^1$ and $R^2$ hydrogen;
$R^3$ is alkyl;
$R^4$ is hydrogen; and
A is =N—.

Another embodiment of the invention are the compounds according to formula I, wherein
A is =CH—.

Another embodiment of the invention are the compounds according to formula I, wherein
$R^1$ is hydrogen, alkoxyalkoxy or acylamino;
$R^2$ is hydrogen;
$R^4$ is hydrogen or alkyl; and
A is =CH—.

Another embodiment of the invention are the compounds according to formula I, wherein
$R^1$ is hydrogen, alkoxyalkoxy or acylamino;
$R^2$ is hydrogen;
$R^3$ is hydrogen;
$R^4$ is hydrogen or alkyl; and
A is =CH—.

Another embodiment of the invention are the compounds according to formula I, wherein
$R^1$ is hydrogen or alkoxyalkoxy;
$R^2$ is hydrogen;
$R^3$ is hydrogen;
$R^4$ is hydrogen or alkyl; and
A is =CH—.

Such compounds, for example, may be selected from the group consisting of:
(2-Methyl-benzyl)-(2-phenyl-1H-pyrrolo[2,3-b]pyridin-5-yl)-amine;
Benzyl-{2-[3-(2-methoxy-ethoxy)-phenyl]-1H-pyrrolo[2,3-b]pyridin-5-yl}-amine;
{2-[3-(2-Methoxy-ethoxy)-phenyl]-1H-pyrrolo[2,3-b]pyridin-5-yl}-(2-methyl-benzyl)-amine; and
Benzyl-(2-phenyl-1H-pyrrolo[2,3-b]pyridin-5-yl)-amine.

Another embodiment of the invention are the compounds according to formula I, wherein
$R^1$ is acylamino;
$R^2$ is hydrogen;
$R^3$ is hydrogen;
$R^4$ hydrogen or alkyl; and
A is =CH—.

Such compounds, for example, may be selected from the group consisting of:

N-[3-(5-Benzylamino-1H-pyrrolo[2,3-b]pyridin-2-yl)-phenyl]-acetamide;

N-{3-[5-(2-Methyl-benzylamino)-1H-pyrrolo[2,3-b]pyridin-2-yl]-phenyl}-acetamide;

N-[4-(5-Benzylamino-1H-pyrrolo[2,3-b]pyridin-2-yl)-phenyl]-acetamide; and

N-{4-[5-(2-Methyl-benzylamino)-1H-pyrrolo[2,3-b]pyridin-2-yl]-phenyl}-acetamide.

Still another embodiment of the invention is a process for the manufacture of the compounds of formula I, wherein (a) the compound of formula VI

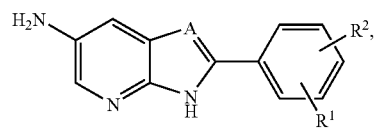

formula VI wherein A, $R^1$ and $R^2$ have the significance as given in formula I above, is reacted with a compound of formula VII

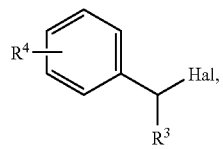

formula VII wherein $R^3$ and $R^4$ have the significance given above for formula I and Hal is bromine or iodine, to give the respective compound of formula I, (b) said compound of formula I is isolated from the reaction mixture, and (c) if desired, converted into a pharmaceutically acceptable salt.

Still another embodiment of the invention is a process for the manufacture of the compounds of formula I in which $R^3$ is hydrogen, wherein (a) the compound of formula VI

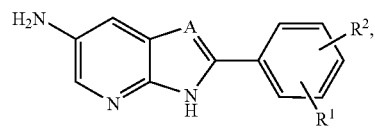

formula VI wherein A, $R^1$ and $R^2$ have the significance as given in formula I above, is reacted with a compound of formula VIII

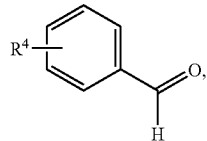

formula VIII wherein $R^4$ has the significance given above for formula I, to give the respective compound of formula I, wherein $R^3$ is hydrogen;

(b) said compound of formula I is isolated from the reaction mixture, and (c) if desired, converted into a pharmaceutically acceptable salt.

The derivatives of the general formula I or a pharmaceutically acceptable salt thereof, may be prepared by any process known to be applicable for the preparation of chemically-related compounds by the one skilled in the art. Such processes, when used to prepare the derivatives of formula I, or a pharmaceutically-acceptable salt thereof, are provided as a further feature of the invention and are illustrated by the following representative examples of Scheme 1 or Scheme 2, in which, unless otherwise stated $R^1$, $R^2$, $R^3$ and $R^4$ have the significance given herein before for formula I and A is =N— in Scheme 1 and =CH— in Scheme 2. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

Scheme 1

The manufacture of the compounds of formula I varies according to the nature of "A" in formula I. The compounds of the present invention wherein "A" is =N— can be prepared according to scheme 1, and are named I-A.

Scheme 1 step 1a

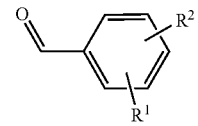

step 1b

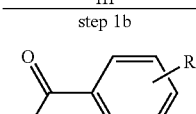

step 2a
Y = Br
step 2b

Y = $NO_2$

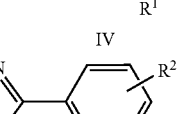
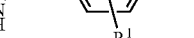

V-A

-continued

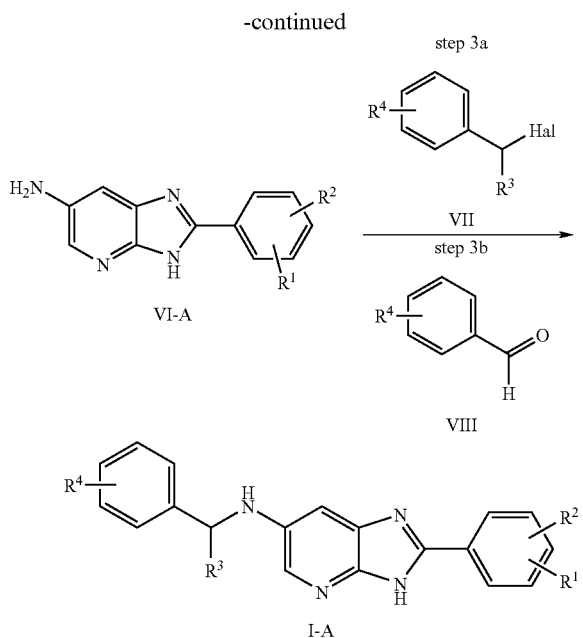

In Scheme 1, $R^1$, $R^2$, $R^3$ and $R^4$ have the significance as given above for formula I, Y is bromine (for the route via step 2a) or nitro (for the route via step 2b) and Hal is bromine or iodine.

Step 1a: Condensation of an aromatic aldehyde of formula III with a 2,3-diamino-pyridine derivative of formula II can carried out at elevated temperatures from 60 to 200° C. in a suitable solvent like acetonitrile, nitrobenzene, dimethylformamide (DMF), dimethylsulfoxide (DMSO), xylene, or methoxyethanol, optionally in the presence of an oxidizing agent like oxygen or an iron (III) salt or sulfur, or 2,3-dichloro-5,6-dicyano-1,4-benzoquinone (DDQ) to give the compounds of formula V-A (wherein A is =N—).

Step 1b: The condensation with an aromatic carboxylic acid of formula IV, or a suitable derivative thereof, with a 2,3-diamino-pyridine derivative of formula II can be achieved at temperatures in the range of 100-220° C. with a condensation reagent like polyphosphoric acid, $POCl_3$, or $P_4O_{10}$, optionally in mixture with methane sulfonic acid to give the compounds of formula V-A (wherein A is =N—).

Step 2a: In the compounds of formula V-A, wherein Y is bromine, such bromine can be replaced by an amino group by heating in aqueous ammonia in the presence of a catalyst like $CuSO_4$ or CuI to give the compounds of formula VI-A. A solubilizing co-solvent like N-methyl-pyrrolidone (NMP) or dimethyl acetamide can be added, and the reaction is carried out at temperatures of 100-180° C. in a closed vessel.

Alternatively, the amino functionality may be introduced in protected form as a tert.-butoxycarbonylamino substituent via coupling under standard Hartwig/Buchwald conditions (for example, with a base like sodium tert. butoxide and a palladium catalyst like $Pd_2(dba)_3$ and a phosphine ligand like tri-tert. butyl phosphane).

Step 2b: For the compounds of formula V-A wherein Y is nitro, the reduction of the nitro group is accomplished by standard conditions such as heterogeneous hydrogenation with Pd on charcoal as the catalyst, in solvents like methanol, ethanol, tetrahydrofuran (THF), or ethyl acetate, at room temperature or up to 80° C.; or by homogeneous hydrogenation with a Pd catalyst and triethyl ammonium formate in a solvent like methanol at reflux conditions. The reduction can also be carried out with base metals like iron or tin in acidic media like acetic acid or aqueous or ethanolic HCl, from room temperature to 120° C. Another suitable reductant would be ammonium sulfide in water or methanol, or tin (II) chloride in dimethylformamide (DMF) or in aqueous HCl. This reduction reaction yields the corresponding the compounds of formula VI-A.

Step 3a: Alkylation of the amino moiety on the compounds of formula VI-A can be done with an appropriate benzyl bromide or iodide of formula VII in an inert solvent like dimethyl formamide, dichloromethane, toluene, tetrahydrofuran (THF), dimethylformamide (DMF), or dimethyl acetamide, optionally in the presence of a base like pyridine, triethyl amine, or di-isopropyl ethyl amine yielding the compounds of formula I-A. Suitable temperatures are in the range of −20° C. to 100° C.

Step 3b: Alternatively, for the compounds of formula VI-A wherein $R^3$ is hydrogen, an appropriate benzaldehyde can be used under conditions of a reductive alkylation, e.g in the presence of a reducing agent like sodium borohydride or sodium cyanoborohydride in a solvent like tetrahydrofuran (THF), methanol, dimethylformamide (DMF), or in the presence of metals like zinc or tin in acetic acid. The intermediate Schiff base can also be formed and isolated from the aldehyde and the heterocyclic amine in a separate step, for instance by condensation under acid catalysis by toluene sulfonic acid with azeotropic removal of water in toluene, benzene, or chloroform, or by condensation in the presence of boron trifluoride or titanium tetrachloride. The Schiff base can subsequently be reduced by the reducing agents named above, or by lithium aluminum hydride in ether or THF, or by catalytic hydrogenation over palladium catalysts in inert solvents like THF, ethyl acetate, or methanol. Thus the compounds of formula I-A, wherein $R^3$ is hydrogen, are obtained.

Scheme 2

The manufacture of the compounds of formula I varies according to the nature of "A" in formula I. The compounds of the present invention wherein "A" is =CH— can be prepared according to scheme 2, and are named I-B.

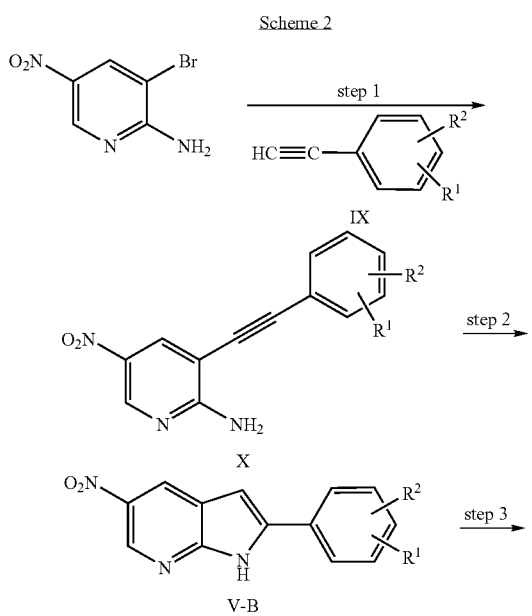

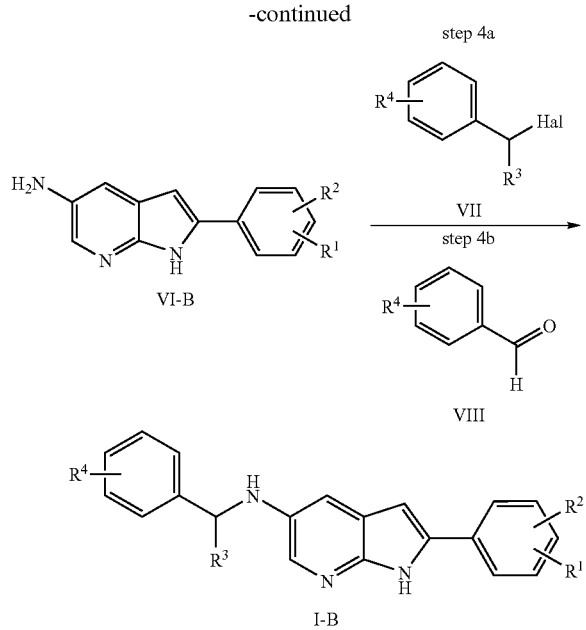

In scheme 2, $R^1$, $R^2$, $R^3$ and $R^4$ have the significance as given above for formula I and Hal is bromine or iodine.

Step 1: An ethynyl-arene of formula IX can be coupled with 2-amino-3-bromo-5-nitropyridine under standard conditions of the so called Sonogashira reaction, with a copper catalyst like CuI or CuCl, and a palladium catalyst like $PdCl_2(PPh_3)_2$ or $PdCl_2(PhCN)_2/PtBu_3$, and a base like triethyl amine or di-isopropyl amine, in an inert solvent like tetrahydrofuran (THF), dioxane, dimethylformamide (DMF), or acetonitrile. The reaction proceeds at room temperature or higher, up to 160° C. to yield the corresponding compounds of formula X.

Alternatively, the ethynyl-arene of formula IX may first be converted into a more reactive alkynyl-Zn or -Sn derivative by procedures known in the art: the ethynyl-arene is deprotonated with a strong base like butyl lithium to form an alkynyl-Li intermediate which is reacted with $ZnCl_2$ or $Bu_3SnCl$ to yield the desired zinc or tin intermediate. These may subsequently be coupled to the bromopyridine under standard cross coupling conditions, for instance by catalysis by a palladium phosphine complex like $Pd(PPh_3)_4$ or $PdCl_2(PPh_3)_2$ or $Pd_2(dba)_3/PtBu_3$ in solvents like dimethyl acetamide, THF, or toluene.

Step 2: Cyclisation of the alkyne intermediates of formula X to give the pyrroles of formula V-B can be achieved by treatment with a base like potassium tert-butoxide, potassium hydride, or sodium ethoxide in an inert solvent like N-methylpyrrolidone (NMP), tetrahydrofuran (THF), dimethylformamide (DMF), or ethanol, at temperatures in the range from room temperature to reflux. Alternatively, the base can be replaced by a catalyst like CuI. The obtained pyrroles of formula V-B can then be converted to compounds of formula I-B according to Step 3 and Step 4a or 4b.

Step 3, Step 4a and Step 4b: These step are analogous to Step 2b, Step 3a and Step 3b which are described under Scheme 1 above.

Certain substituents in the formulas I-A or I-B may not be inert to the conditions of the synthesis sequences described above and may require protection by standard protecting groups known in the art. For instance, an amino maybe protected as a tert.-butoxycarbonyl derivative. Alternatively, some substituents may be derived from others at the end of the reaction sequence. For instance, a compound of formula I may be synthesized bearing a nitro group, which substituents are finally converted to an acylamino substituent by standard procedures.

The compounds of the general formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide, especially from sodium. The chemical modification of a pharmaceutical compound into a salt is a technique well known to pharmaceutical chemists in order to obtain improved physical and chemical stability, hygroscopicity, flowability and solubility of compounds. It is for example described in Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically acceptable, inorganic or organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

An embodiment of the invention is a pharmaceutical composition containing one or more compounds according to formula I as active ingredients together with pharmaceutically acceptable carriers.

Another embodiment of the invention is said pharmaceutical composition for the treatment of diseases mediated by an inappropriate activation of src family tyrosine kinases.

Another embodiment of the invention is said pharmaceutical composition for the treatment of inflammatory-, immunological-, CNS disorders or bone diseases.

Another embodiment of the invention is said pharmaceutical composition for the treatment of cancer.

Another embodiment of the invention is said pharmaceutical composition for the treatment of colorectal cancer, breast cancer, lung cancer, prostate cancer, pancreatic cancer, gastric cancer, bladder cancer, ovarian cancer, melanoma, neuroblastoma, cervical cancer, kidney cancer or renal cancer, leukemias or lymphomas.

Another embodiment of the invention is the use of one or more compounds according to formula I for the manufacture of pharmaceutical compositions for the treatment of cancer.

Another embodiment of the invention is the use of one or more compounds according to formula I for the manufacture of pharmaceutical compositions for the treatment of colorectal cancer, breast cancer, lung cancer, prostate cancer, pancreatic cancer, gastric cancer, bladder cancer, ovarian cancer, melanoma, neuroblastoma, cervical cancer, kidney cancer or renal cancer, leukemias or lymphomas.

Another embodiment of the invention is the use of one or more compounds according to formula I for the manufacture of pharmaceutical compositions for the treatment of inflammatory-, immunological-, CNS disorders or bone diseases.

Another embodiment of the invention is the use of one or more compounds according to formula I as src family tyrosine kinase inhibitors.

Another embodiment of the invention is the use of one or more compounds according to formula I as cell signaling-regulating and anti-proliferating agents.

Another embodiment of the invention is the use of one or more compounds according to formula I for the treatment of inflammatory-, immunological-, CNS disorders or bone diseases.

Another embodiment of the invention is the use of one or more compounds of formula I according to formula I for the treatment of cancer.

Another embodiment of the invention is a pharmaceutical composition comprising a therapeutically effective amount of a compound according to formula I as active ingredients and a pharmaceutically acceptable carrier.

Another embodiment of the invention is a method of treating cancer comprising administering to a person in need thereof a therapeutically effective amount of a compound according to formula I.

Another embodiment of the invention is a method of treating colorectal cancer, breast cancer, lung cancer, prostate cancer, pancreatic cancer, gastric cancer, bladder cancer, ovarian cancer, melanoma, neuroblastoma, cervical cancer, kidney cancer or renal cancer, leukemias or lymphomas comprising administering to a person in need thereof a therapeutically effective amount of a compound according to formula I.

A pharmaceutical preparation was obtained e.g. by using the following procedure:
1. Weigh 4.0 g glass beads in custom made tube GL 25, 4 cm (the beads fill half of the tube).
2. Add 50 mg compound, disperse with spatulum and vortex.
3. Add 2 mL gelatin solution (weight beads:gelatin solution=2:1) and vortex.
4. Cap and wrap in aluminum foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes(here 1 mL steps) until final volume is reached or extract is clear.
10. Fill up to final volume with gelatin and homogenise.

The above described preparation yields micro-suspensions of the compounds of formula I with particle sizes between 1 and 10 µm. The suspensions are suitable for oral applications and were used in the in vivo pharmacokinetic testings described below.

Pharmacological Activity:

The activity of the compounds according to this invention as inhibitors for the src-family tyrosine kinases was shown by using the following assay.

SRC-Inhibitor-Assay Parameters:

| Reaction mixture: | |
|---|---|
| ATP | 5 µM |
| Peptide   (Ro + Ja133-Ro): | 10 µM |
|    Ja133-Ro | 196 nM |
|    Ro | 9.8 µM |
| PT66 | 230 ng/mL |
| Assay buffer: | 4 mM MgCl2 |
|  | 2 mM TCEP |
|  | 50 mM HEPES |
|  | 0.1% Tween 20 |
|  | pH 7.3 |
| Enzyme: | 2.5 U/mL |
| Inhibitor: | max. 25 µM |
|  | min. 0.42 nM |

Material:
Eu-labelled phosphotyrosine antibody:—for Lck Cisbio Mab PT66-K,
for Src EG&G Wallac PT66 Eu-W1024 (all commercially available).
Peptides: Ro: $NH_2$-A-E-E-E-I-Y-G-E-F-E-A-K-K-K-K-$CONH_2$, and
Ja133-Ro: Ja133-G-Aminocaprylic acid-A-E-E-E-I-Y-G-E-F-E-A-K-K-K-K-$CONH_2$, wherein Ja133 is Light-Cycler-Red 640-N-hydroxy succinimide ester;
whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 µmol scale) of a Rink-Linker modified polystyrene solid phase by repeatedly conjugating an twenty fold excess of amino acids each protected by temporary piperidine labile Fmoc- and permanent acid labile tert-Bu-, BOC- and O-tert-Bu-groups depending on the side chain function. The substrate sequence AEEEIYGEFEAKKKK was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased from Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoroacetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0].

Enzymes: Upstate Lck (p56$^{lck}$, active), Upstate Src (p60$^{c-src}$, partially purified) were purchased from UBI, Upstate Biotech, Inc.

Time-resolved Fluorescence Assay: Reader: Perkin Elmer, Wallac Viktor 1420-040 multilabel counter; Liquid handling system: Beckman Coulter, Biomek 2000.

ATP, Tween™ 20, 4-(2-hydroxyethyl)-1-piperazineethanesulfonic acid (HEPES) were purchased from Roche Molecular Biochemicals, $MgCl_2$ and $MnCl_2$ were purchased from Merck Eurolab, Tris(2-carboxyethyl)phosphine hydrochloride (TCEP) was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (XLfit software (ID Business Solution Ltd., Guilford, Surrey, UK))

| Example-No. | IC50 src [μM] |
|---|---|
| 2-6 | 0.031 |
| 2-2 | 0.131 |
| 2-3, 2-4, 2-5, 2-7, 2-8, | 0.010-0.500 |
| 1-1, 2-1 | 0.500-1.500 |

| Example-No. | IC50 lck [μM] |
|---|---|
| 2-6 | 0.223 |
| 2-2 | 0.757 |
| 2-1, 2-4, 2-5, 2-7, 2-8, | 0.10-1.00 |
| 1-1, 2-3 | 1.00-5.00 |

The following examples and references are provided to aid the understanding of the present invention, the true scope of which is set forth in the appended claims. It is understood that modifications can be made in the procedures set forth without departing from the spirit of the invention.

Experimental Procedures

Starting Materials 2-phenyl-3H-imidazo[4,5-b]pyridin-6-ylamine a) 6-Nitro-2-phenyl-3H-imidazo[4,5-b]pyridine 14.05 g 2,3-diamino-5-nitropyridine and 9.68 g benzaldehyde in 250 mL nitrobenzene were heated to 140-150° C. for 15 hours (hrs). The solvent is removed by vacuum distillation and the residue is dispersed in ethyl acetate, filtered, and the filter residue washed thoroughly with ethyl acetate.

Yield 16.0 g b) 2-phenyl-3H-imidazo[4,5-b]pyridin-6-ylamine 12.0 g 6-nitro-2-phenyl-3H-imidazo[4,5-b]pyridine were dissolved in 1 L acetic acid. 18 g iron powder were added and the mixture heated to 80° C. with stirring. After 2 hrs the mixture was cooled to room temperature and filtered over Celite. The celite pad was washed with methanol and the combined filtrates were evaporated. The residue was dissolved methanol/dichloromethane 1:1 and filtered over silica. The filtrate was concentrated to a volume of 100 mL, the resulting precipitate collected by filtration and washed with methanol.

Yield 7.68 g

Substituted Phenyl-Acetylenes

Substituted phenyl-acetylenes were prepared by acylation of 3- or 4-amino-phenylacetylene by literature procedures, as described in U.S. Pat. No. 4,162,265A, or by alkylation of 3- or 4-hydroxyphenylacetylene by literature procedures. For instance, 3-(2-methoxyethoxy)phenylacetylene 3-Hydroxyphenylacetylene (237 mg, 2 mmol) was heated with 2-bromoethylmethylether (0.23 mL, 2.4 mmol) and potassium carbonate (322 mg, 2.4 mmol) in acetone (5 mL) to 110° C. in a microwave oven (CEM Discover) for 45 minutes. Water (1 mL) was added to the mixture and the whole was extracted with dichloromethane (2×25 mL). The combined organics were dried over $MgSO_4$, filtered and concentrated in vacuo to afford a brown oil. The oil was purified by column chromatography ($SiO_2$, dichloromethane) to afford 3-(2-methoxyethoxy)phenylacetylene as a colourless oil (247mg, 70% yield).

$^1$H-NMR (400 MHz; $CDCl_3$): 7.23 (1H, dd, J 8.8, 8.0), 7.08 (1H, dt, J 7.6, 1.2), 7.04 (1H, dd, J 1.48, 2.7), 6.94 (1H, ddd, J 1.0, 2.6, 8.3), 4.11 (2H, t, J 4.6), 3.74 (2H, t, J 4.6), 3.45 (3H, s), 3.05 (1H, s).

Alternatively, 4-(2-methoxyethoxy)phenylacetylene was prepared from the corresponding iodobenzene and trimethylsilylacetylene by Sonogashira coupling, as described for 4-methoxyphenylacetylene in Tsuji, M., J. Org. Chem. 68 (2003) 9589-9597-supporting information S.1-36 -http://pubs.acs.org/subscribe/journals/joceah/suppinfo/jo035090f/jo035090fsi2003 0918__025110.pdf.

3-(acetylamino)phenylacetylene

Acetic anhydride (13.8 mL, 144 mmol) was added dropwise to a solution of 3-ethynylaniline (14.0 g, 120 mmol) and 4-(Dimethylamino-)pyridine (DMAP) (1.5 g, 12 mmol) in tetrahydrofuran (300 mL). The mixture was stirred at room temperature for 2 hours, water (100 mL) was added to the mixture and the whole was extracted with dichloromethane (2×250 mL). The combined organics was washed with 10% citric acid (100 mL) followed by saturated sodium bicarbonate solution (100 mL), dried over MgSO$_4$, filtered and concentrated in vacuo to afford 3-(acetylamino)phenylacetylene as a yellow solid (18.3 g, 96%).

$^1$H-NMR (400 MHz; CDCL$_3$): 7.62 (1H, s), 7.53 (1H, d, J 7.7), 7.41 (1H, br.s), 7.28-7.22 (2H, m), 3.06 (1H, s), 2.17 (3H, s).

Final Products

Example 1-1

(1-Phenyl-ethyl)-(2-phenyl-3H-imidazo[4,5-b]pyridin-6-yl)-amine 100 mg 2-phenyl-3H-imidazo[4,5-b]pyridin-6-ylamine from ex. b) were dissolved in 1 mL dry dimethylformamide (DMF) and 92 mg 1-phenylethyl bromide were added at room temperature. The mixture was stirred for 18 hours (hrs), the DMF was removed under vacuum and the residue purified by chromatography on silica eluting stepwise first with dichloromethane, then dichloromethane/methanol (60:1), then dichloromethane/methanol/ammonia (60:1:0,2). Product containing fractions were pooled and further purified by preparative HPLC-MS.

Yield 17.4 mg of the title product.

$^1$H-NMR (400 MHz, D6-DMSO): 8.08 (d; 2H); 7.93 (s, 1H); 7.53-7.43 (m, 6H); 7.33 (t, 2H); 7.20 (t, 1H); 6.79 (br s, 1H); 6.40 (br s, 1H); 4.55 (br s, 1H); 1.49 (d, 3H).

Example 2-1

Benzyl-{2-[3-(2-methoxy-ethoxy)-phenyl]-1H-pyrrolo[2,3-b]pyridin-5-yl}-amine a) 3-[3-(2-methoxy-ethoxy)-phenylethynyl]-5-nitro-pyridin-2-ylamine 3-(2-Methoxy-ethoxy)-phenylacetylene (6.3 g, 36 mmol) was added to a solution of triethylamine (1.92 mL, 14 mmol), 2-amino-3-bromo-5-nitropyridine (4 g, 18 mmol), PdCl$_2$(PPh$_3$)$_2$ (966 mg, 1.38 mmol) and CuI (262 mg, 1.38 mmol) in anhydrous tetrahydrofuran (80 mL) in the dark. The mixture was stirred at room temperature for 48 hours then concentrated in vacuo and resolvated in dichloromethane (150 mL). The organic solution was washed with water (25 mL), dried over MgSO4, filtered and concentrated in vacuo to 20% of its original volume and heptane (20 mL) was then added. The resultant yellow solid was filtered and dried to give 3-[3-(2-methoxy-ethoxy)-phenylethynyl]-5-nitro-pyridin-2-ylamine (4.2 g, 74% yield).

$^1$H-NMR (400 MHz; d$^6$-DMSO): 8.89 (1H, d, J 2.7), 8.34 (1H, d, J 2.7), 7.39 (1H, m), 7.35 (1H, d, J 8.0), 7.30 (1H, dt, J 1.0, 7.6), 7.04 (1H, ddd, J 1.0, 2.6, 8.2), 4.15 (2H, t, J 4.5), 3.69 (2H, t, J 4.5), 3.34 (3H, s).

MS: M=(ES+) 314 (M+H), 355 (M+acetonitrile)

b) 2-[3-(2-methoxy-ethoxy)-phenyl]-5-nitro-1H-pyrrolo[2,3-b]pyridine

Potassium tert-butoxide (1.18 g, 10.5 mmol) was added to a solution of 3-[3-(2-methoxy-ethoxy)-phenylethynyl]-5-nitro-pyridin-2-ylamine (1.57 g, 5 mmol) in a 2:1 mixture of tetrahydrofuran and dimethylformamide (75 mL). The mixture was heated at 70° C. for 16 hours then the tetrahydrofuran was removed in vacuo. The mixture was poured onto a pad of silica and eluted with ethyl acetate then 10% methanol in ethyl acetate. The organics were concentrated in vacuo to 5% of their original volume and water (30 mL) was added. The resultant orange solid was filtered and dried to afford 2-[3-(2-methoxy-ethoxy)-phenyl]-5-nitro-1H-pyrrolo[2,3-b]pyridine (1.3 g, 83%).

$^1$H-NMR (400 MHz): d$^6$-DMSO): 12.88 (1H, s), 9.04 (1H, d, J 2.6), 8.77 (1H, d, J 2.6), 7.52-7.50 (2H, m), 7.36 (1H, app. t, J 8.1, 7.8), 7.18 (1H, s), 6.95 (1H, dd, J 1.8, 8.1), 4.15 (2H, t, J 4.6), 3.65 (2H, t, J 4.6), 3.25 (3H, s).

MS: M=(ES+) 314 (M+H), 355 (M+acetonitrile)

c) 2-[3-(2-methoxy-ethoxy)-phenyl]-1H-pyrrolo[2,3-b]pyridin-5-ylamine

To a mixture of 2-[3-(2-methoxy-ethoxy)-phenyl]-5-nitro-1H-pyrrolo[2,3-b]pyridine (7.1 mmol, 2.2 g) and iron powder (6.7 g) in ethanol (50 mL) was added HCl (conc) (0.7 mL) and water (5 mL). The mixture was heated at 70° C. for 3 hours then cooled and filtered through Celite®. The solvent was removed in vacuo and the residue resolved in ethyl acetate (30 mL), washed with saturated sodium bicarbonate (15 mL), dried over MgSO4, filtered and concentrated in vacuo. The crude product was purified by column chromatography (SiO$_2$, ethyl acetate) to afford 2-[3-(2-methoxy-ethoxy)-phenyl]-1H-pyrrolo[2,3-b]pyridin-5-ylamine (1.2 g, 60%).

$^1$H-NMR (400 MHz; d$^6$-DMSO): 11.62 (1H, s), 7.78 (1H, d, J 2.0), 7.53-7.50 (2H, m), 7.38 (1H, app. t, J 8.0), 7.13 (1H, d, J 2.3), 6.93 (1H, dd, J 1.7, 8.0), 6.75 (1H, d, J 2.0), 4.8 (2H, br.s), 4.24 (2H, t, J 4.6), 3.76 (2H, t, J 4.6), 3.40 (3H, s).

MS: M=(ES+) 284 (M+H)

d) Benzyl-{2-[3-(2-methoxy-ethoxy)-phenyl]-1H-pyrrolo[2,3-b]pyridin-5-yl}-amine

Polymer supported borohydride (706 mg, 1.8 mmol) was added to a mixture of 2-[3-(2-methoxy-ethoxy)-phenyl]-1H-pyrrolo[2,3-b]pyridin-5-ylamine (50 mg, 0.18 mmol) and benzaldehyde (18mg, 0.18 mmol) in methanol (3 mL). The mixture was stirred for 16 hours, filtered, concentrated in vacuo and purified by preparative HPLC to afford benzyl-{2-[3-(2-methoxy-ethoxy)-phenyl]-1H-pyrrolo[2,3-b]pyridin-5-yl}-amine (4.4 mg, 7%)

MS: M=(ES+) 374 (M+H), 415 (M+acetonitrile), 747 (2M+H)

Using the experimental conditions reported above (Example 2-1) and the appropriate starting materials, the following derivatives were prepared:

| Example No. | Systematic name | $^1$H-NMR |
| --- | --- | --- |
| 2-1 | Benzyl-{2-[3-(2-methoxy-ethoxy)-phenyl]-1H-pyrrolo[2,3-b]pyridin-5-yl}-amine | (400 MHz, D6-DMSO) 11.61 (s, 1H); 7.81 (d; 1H); 7.45-7.40 (m, 4H); 7.35-7.29 (m, 3H); 7.23 (t, 1H); 6.96 (d, 1H); 6.86 (dd, 1H); 6.67 (d, 1H); 5.99 (t, 1H); 4.31 (d, 2H); 4.17 (t, 2H); 3.69 (t, 2H); 3.33 (s, not separated from dmso). |

-continued

| Example No. | Systematic name | ¹H-NMR |
|---|---|---|
| 2-2 | {2-[3-(2-Methoxy-ethoxy)-phenyl]-1H-pyrrolo[2,3-b]pyridin-5-yl}-(2-methyl-benzyl)-amine | (400 MHz, D6-DMSO) 11.62 (s, 1H); 7.84 (d; 1H); 7.46-7.42 (dd, 2H); 7.34-7.29 (m, 2H); 7.18 (t, 1H); 7.16-7.13 (m, 2H); 6.97 (d, 1H); 6.87 (dd, 1H); 6.69 (d, 1H); 5.80 (t, 1H); 4.25 (d, 2H); 4.17 (t, 2H); 3.70 (t, 2H); 3.33 (s, not separated from dmso); 2.36 (s, 3H). |
| 2-3 | Benzyl-(2-phenyl-1H-pyrrolo[2,3-b]pyridin-5-yl)-amine | (400 MHz, D6-DMSO) 11.64 (s, 1H); 7.86-7.81 (dd; 3H); 7.44-7.40 (dd, 4H); 7.35-7.21 (m, 4H); 6.97 (d, 1H); 6.65 (s, 1H); 5.99 (t, 1H); 4.31 (d, 2H). |
| 2-4 | (2-Methyl-benzyl)-(2-phenyl-1H-pyrrolo[2,3-b]pyridin-5-yl)-amine | no data! |
| 2-5 | N-[3-(5-Benzylamino-1H-pyrrolo[2,3-b]pyridin-2-yl)-phenyl]-acetamide | (400 MHz, D6-DMSO) 11.62 (s, 1H); 10.01 (s, 1H); 7.99 (s; 1H); 7.81 (d, 1H); 7.50 (t, 2H); 7.42 (d, 2H); 7.36-7.31 (m, 3H); 7.23 (d, 1H); 7.00 (d, 1H); 6.50 (d, 1H); 5.97 (t, 1H); 4.31 (d, 2H); 2.07 (s, 3H). |
| 2-6 | N-{3-[5-(2-Methyl-benzylamino)-1H-pyrrolo[2,3-b]pyridin-2-yl]-phenyl}-acetamide | (400 MHz, D6-DMSO) 11.64 (s, 1H); 10.01 (s, 1H); 7.99 (s; 1H); 7.84 (d, 1H); 7.51 (t, 2H); 7.34 (t, 2H); 7.19 (dt, 1H); 7.16-7.11 (m, 2H); 7.01 (d, 1H); 6.51 (d, 1H); 5.78 (t, 1H); 4.25 (d, 2H); 2.37 (s, 3H); 2.07 (s, 3H). |
| 2-7 | N-[4-(5-Benzylamino-1H-pyrrolo[2,3-b]pyridin-2-yl)-phenyl]-acetamide | (400 MHz, D6-DMSO) 11.53 (s, 1H); 10.04 (s, 1H); 7.78-7.75 (dd; 3H); 7.62 (d, 2H); 7.42 (d, 2H); 7.33 (t, 2H); 7.23 (t, 1H); 6.95 (d, 1H); 6.55 (d, 1H); 5.95 (t, 1H); 4.30 (d, 2H); 2.06 (s, 3H). |
| 2-8 | N-{4-[5-(2-Methyl-benzylamino)-1H-pyrrolo[2,3-b]pyridin-2-yl]-phenyl}-acetamide | (400 MHz, D6-DMSO) 11.54 (s, 1H); 10.04 (s, 1H); 7.80-7.76 (dd; 3H); 7.62 (d, 2H); 7.33 (dd, 1H); 7.19 (dt, 1H); 7.16-7.11 (m, 2H); 6.96 (d, 1H); 6.57 (d, 1H); 5.76 (t, 1H); 4.24 (d, 2H); 2.36 (s, 3H); 2.06 (s, 3H). |

In the preparation of the intermediate N-[3-(5-nitro-1H-pyrrolo[2,3-b]pyridin-2-yl)-phenyl]-acetamide of the examples the 2-5 to 2-8 by cyclysation reaction an higher equimolar amount of base (Potassium tert-butoxide) as in Example 2-1 is needed.

Preparation of N-[3-(5-nitro-1H-pyrrolo[2,3-b]pyridin-2-yl)-phenyl]-acetamide

Potassium tert-butoxide (2.25 g, 20 mmol) was added to a solution of N-[4-(2-amino-5-nitro-pyridin-3-ylethynyl)-phenyl]-acetamide (1.48 g, 5 mmol) in a 2:1 mixture of tetrahydrofuran and dimethylformamide (75 mL). The mixture was heated at 70° C. for 16 hours then the tetrahydrofuran was removed in vacuo. The mixture was poured onto a pad of silica and eluted with 10% methanol in ethyl acetate. The organics were concentrated in vacuo to 5% of their original volume and water (30 mL) was added. The resultant orange solid was filtered and dried to afford N-[3-(5-Nitro-1H-pyrrolo[2,3-b]pyridin-2-yl)-phenyl]-acetamide (1.01 g, 68%).

¹H-NMR (400 MHz; d⁶-DMSO): 12.97 (1H, s), 10.17 (1H, s), 9.16 (1H, d, J 2.5), 8.94 (1H, d, J 2.5), 8.24 (1H, s), 7.70 (1H, d, J 7.8), 7.63 (1H, d, J 8.2), 7.50 (1H, app. t, J 7.9), 7.10 (1H, s), 2.15 (3H, s).

MS: M=(ES+) 297 (M+H), 338 (M+acetonitrile), 593 (2M+H), 889 (3M+H)

The invention claimed is:
1. A compound according to formula I,

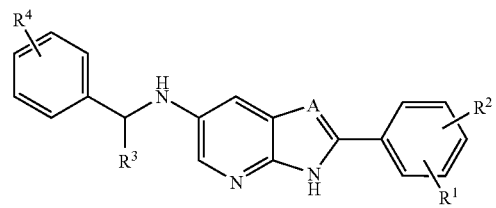

formula I wherein,
$R^1$ and $R^2$ independently represent hydrogen, halogen, alkyl, alkoxy, alkoxyalkoxy or acylamino;
$R^3$ is hydrogen or alkyl;
$R^4$ is hydrogen, halogen, alkoxy or alkyl;
A is =CH— or =N—;
and all pharmaceutically acceptable salts thereof.

2. The compounds according to claim 1, wherein
$R^1$ is hydrogen, alkoxyalkoxy or acylamino;
$R^2$ is hydrogen; and
$R^4$ is hydrogen or alkyl.

3. The compounds according to claim 1, wherein
$R^1$ and $R^2$ independently represent hydrogen or alkyl;
$R^3$ is hydrogen or alkyl;
$R^4$ is hydrogen or alkyl; and
A is =N—.

4. The compounds according to any one of claim 1 or 2, wherein
R$^1$ is hydrogen, alkoxyalkoxy or acylamino;
R$^2$ is hydrogen;
R$^3$ is hydrogen;
R$^4$ is hydrogen or alkyl; and
A is =CH—.

5. The compounds according to claim 1, selected from the group consisting of:
 (1-Phenyl-ethyl)-(2-phenyl-3H-imidazo[4,5-b]pyridin-6-yl)-amine;
 Benzyl-{2-[3-(2-methoxy-ethoxy)-phenyl]-1H-pyrrolo[2,3-b]pyridin-5-yl}-amine;
 {2-[3-(2-Methoxy-ethoxy)-phenyl]-1H-pyrrolo[2,3-b]pyridin-5-yl}-(2-methyl-benzyl)-amine;
 Benzyl-(2-phenyl-1H-pyrrolo[2,3-b]pyridin-5-yl)-amine;
 (2-Methyl-benzyl)-(2-phenyl-1H-pyrrolo[2,3-b]pyridin-5-yl)-amine;
 N-[3-(5-Benzylamino-1H-pyrrolo[2,3-b]pyridin-2-yl)-phenyl]-acetamide;
 N-{3-[5-(2-Methyl-benzylamino)-1H-pyrrolo[2,3-b]pyridin-2-yl]-phenyl}-acetamide;
 N-[4-(5-Benzylamino-1H-pyrrolo[2,3-b]pyridin-2-yl)-phenyl]-acetamide; and
 N-{4-[5-(2-Methyl-benzylamino)-1H-pyrrolo[2,3-b]pyridin-2-yl]-phenyl}-acetamide.

6. A pharmaceutical composition, containing one or more compounds according to claims 1 to 5 as active ingredients together with pharmaceutically acceptable carriers.

* * * * *